US006518301B1

(12) United States Patent
Barlaam et al.

(10) Patent No.: US 6,518,301 B1
(45) Date of Patent: Feb. 11, 2003

(54) ESTROGEN RECEPTOR-β LIGANDS

(75) Inventors: Bernard Christophe Barlaam, Wilmington, DE (US); Timothy Martin Piser, Wilmington, DE (US)

(73) Assignee: AstraZeneca AB (SE)

( * ) Notice: Subject to any disclaimer, the term of this patent is extended or adjusted under 35 U.S.C. 154(b) by 0 days.

(21) Appl. No.: 09/959,032

(22) PCT Filed: Apr. 11, 2000

(86) PCT No.: PCT/GB00/01380

§ 371 (c)(1),
(2), (4) Date: Jan. 7, 2002

(87) PCT Pub. No.: WO00/62765

PCT Pub. Date: Oct. 26, 2000

Related U.S. Application Data

(60) Provisional application No. 60/129,901, filed on Apr. 16, 1999.

(51) Int. Cl.⁷ .......................... A61K 31/38; A61K 31/35
(52) U.S. Cl. .................... 514/444; 514/456; 514/457
(58) Field of Search ................. 574/456, 457, 574/444

(56) References Cited

U.S. PATENT DOCUMENTS 5,733,926 A    3/1998   Gorbach

FOREIGN PATENT DOCUMENTS

| EP | 0 135 172 A | 3/1985 |
| EP | 0 729 951 A | 9/1996 |
| EP | 0 835 867 A | 4/1998 |
| WO | WO 98 44920 A | 10/1998 |
| WO | WO 98 50026 | 11/1998 |

OTHER PUBLICATIONS

Anderson J J B et al: "bIPHASIC Effects of Genistein on Bone Tissue in the Ovariectomized, Lactating Rat Model" Proceedings of the Society for Experimental Biology & Medicine, US, Academic Press Inc. New York, vol. 217, No. 3, 1998, p. 345–350; Abstract p. 345, col: 1–p. 346, col: 1 Paragraph 2 Figure 1.

J Geller et al: "Genistein Inhibits the Growth of Human–Patient BPH and Prostate Cancer in Histoculture" Prostate, US, Wiley–Liss, New York, NY vol. 2, No. 34, Feb. 1, 1998 pp 75–79, Abstract.

M C Bosland et al: "Inhibition of Human Prostate Cancer Cell Proliferation by Genistein" Proceedings of the Annual Meeting of the American Association for Cancer Research, US, New York, NY No. 38, Mar. 1, 1997, p. 262; Abstract.

Bindal, Rajeshwar D. et al: "1,2–Bis(4–Hydroxyphenyl)–3, 4–Dihydro–6Hydroxynaphthalene, a Photofluorogenic Ligand for the Estrogen Receptor" Photochem, Photobiol. 1986, 43 (2) , 121–6, the Whole Document.

McCague, Raymond et al: "Synthesis and Estrogen Receptor Binding of 6,7–Dihydro–8–Phenyl–9[4–[2–(Dimethylamin 0) Ethoxy]Phenyl]–5H– Benzocycloheptene, a Nonisomjerizable Analog of Tamoxifen. X–ray Crystallographic Studies" J. Med. Chem. (1986) , 29 (10) , 2053–9 the Whole Document.

Vinson J A et al: "Plant Favonoids, especially tea flavonols, are powerful antioxidants using an in vitro oxidation model for heart disease" Journal of Agricultural and food chemistry, US, American Chemical Society, Washington. vol. 43, No. 11; p. 2802, col: 1, paragraph 4 (1995).

*Primary Examiner*—James H. Reamer
(74) *Attorney, Agent, or Firm*—Karen Kendrad

(57) ABSTRACT

A method for treating a disease associated with the estrogen receptor-β, comprising the step of administering a therapeutically-effective amount of a compound that satisfies the equation: $(K_i\alpha_A/K_i\beta_A)/(K_i\alpha_E/K_i\beta_E)>1$, optionally having the general structure (I).

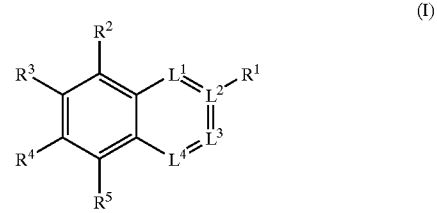

(I)

7 Claims, No Drawings

ESTROGEN RECEPTOR-β LIGANDS

"This is a national stage application under 35 U.S.C. Section 371 of PCT/GB00/01380, filed Apr. 11, 2000" which claims priority of Provisional Application 60,129,901 filed Apr. 16, 1999.

TECHNICAL FIELD

The present invention is directed to a series of ligands, and more particularly to estrogen receptor-β ligands which have better selectivity than estrogen for the estrogen receptor-β over the estrogen receptor-α, as well as to methods for their production and use in the treatment of diseases related to the estrogen receptor-β, specifically. Alzheimer's disease, anxiety disorders, depressive disorders, osteoporosis, cardiovascular disease, rheumatoid arthritis, or prostate cancer.

BACKGROUND

Estrogen-replacement therapy ("ERT") reduces the incidence of Alzheimer's disease and improves cognitive function in Alzheimer's disease patients (Nikolov et al. Drugs of Today, 34(11), 927–933 (1998)). ERT also exhibits beneficial effects in osteoporosis and cardiovascular disease, and may have anxiolytic and anti-depressant therapeutic properties. However, ERT shows detrimental uterine and breast side effects that limit its use.

The beneficial effects of ERT in post-menopausal human women is echoed by beneficial effects of estrogen in models relevant to cognitive function, anxiety, depression, bone loss, and cardiovascular damage in ovariectomized rats. Estrogen also produces uterine and breast hypertrophy in animal models reminiscent of its mitogenic effects on these tissues in humans.

The beneficial effects of ERT in post-menopausal human women is echoed by beneficial effects of estrogen in models relevant to cognitive function, anxiety, depression, bone loss, and cardiovascular damage in ovariectomized rats. Specifically, experimental studies have demonstrated that estrogen effects the central nervous system ("CNS") by increasing cholinergic function, increasing neurotrophin/neurotrophin receptor expression, altering amyloid precursor protein processing, providing neuroprotection against a variety of insults, and increasing glutamatergic synaptic transmission, among other effects. The overall CNS profile of estrogen effects in pre-clinical studies is consistent with its clinical utility in improving cognitive function and delaying Alzheimer's disease progression. Estrogen also produces mitogenic effects in uterine and breast tissue indicative of its detrimental side effects on these tissues in humans.

The estrogen receptor ("ER") in humans, rats, and mice exists as two subtypes. ER-α and ER-β, which share about a 50% identity in the ligand-binding domain (Kuiper et al. Endocrinology 139(10) 4252–4263 (1998)). The difference in the identity of the subtypes accounts for the fact that some small compounds have been shown to bind preferentially to one subtype over the other (Kuiper et al.).

In rats. ER-β is strongly expressed in brain, bone and vascular epithelium, but weakly expressed in uterus and breast, relative to ER-α. Furthermore, ER-α knockout (ERKO-α) mice are sterile and exhibit little or no evidence of hormone responsiveness of reproductive tissues. In contrast, ER-β knockout (ERKO-β) mice are fertile, and exhibit normal development and function of breast and uterine tissue. These observations suggest that selectively targeting ER-β over ER-α could confer beneficial effects in several important human diseases, such as Alzheimer's disease, anxiety disorders, depressive disorders, osteoporosis, and cardiovascular disease without the liability of reproductive system side effects. Selective effects on ER-β-expressing tissues (CNS, bone, etc.) over uterus and breast could be achieved by agents that selectively interact with ER-β over ER-α.

It is a purpose of this invention to identify ER-β-selective ligands that are useful in treating diseases in which ERT has therapeutic benefits.

It is another purpose of this invention to identify ER-β-selective ligands that mimic the beneficial effects of ERT on brain, bone and cardiovascular function.

It is another purpose of this invention to identify ER-β-selective ligands that increase cognitive function and delay Alzheimer's disease progression.

SUMMARY OF THE INVENTION

This present invention is directed to the use of compounds having the generic structure:

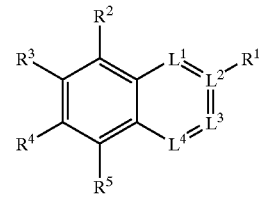

as ER-β-selective ligands, which mimic ERT, but lack undesirable side effects of ERT. These compounds particularly satisfy the formula:

$$(K_{i\alpha A}/K_{i\beta A})/(K_{i\alpha E}/K_{i\beta E}) > 1,$$

preferably:

$$(K_{i\alpha A}/K_{i\beta A})/(K_{i\alpha E}/K_{i\beta E}) > 30,$$

more preferably:

$$(K_{i\alpha A}/K_{i\beta A})(K_{i\alpha E}/K_{i\beta E}) > 100,$$

wherein $K_{i\alpha A}$ is the $K_i$ value for the ligand in ER-α; $K_{i\beta A}$ is the Ki value for the ligand in ER-α: $K_{i\alpha E}$ is the $K_i$ value for estrogen in ER-α; and $K_{i\beta E}$ is the $K_i$ value for estrogen in ER-β.

DETAILED DESCRIPTION OF THE INVENTION

The instant invention involves a method for treating a disease associated with the estrogen receptor-β, comprising the step of administering a therapeutically-effective amount of a compound that satisfies the equation $(K_{i\alpha A}/K_{i\beta A})/(K_{i\alpha E}/K_{i\beta E}) > 1$, wherein $K_{i\alpha A}$ is the $K_i$ value for the agonist in ER-α; $K_{i\beta A}$ is the $K_i$ value for the agonist in ER-β; $K_{i\alpha E}$ is the $K_i$ value for estrogen in ER-α; and $K_{i\beta E}$ is the $K_i$ value for estrogen in ER-β. Preferably, the compound satisfies the equation $(K_{i\alpha A}/Ki_{\alpha A})/(K_{i\alpha E}/K_{i\beta E}) > 100$. Preferred diseases associated with the estrogen receptors β are selected from Alzheimer's disease, anxiety disorders, depressive disorders, osteoporosis, cardiovascular disease, rheumatoid arthritis and prostate cancer. More preferably, the diseases are Alzheimer's disease or depressive disorders.

The compounds of the instant invention are ER-β-selective ligands of the structure:

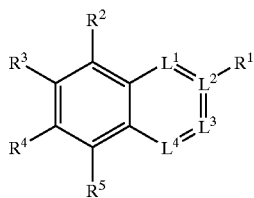

In this structure $L^1$ is —C(=O)—, =C($R^6$)—, —CH($R^6$)—, O, S, or N$R^a$, preferably —C(=O)—, =C($R^6$)—, —CH($R^6$)—or O; $L^2$ is =C—or —CH—; $L^3$ is =C($R^6$)—, —CH($R^6$)—or —C(=O)—; and $L^4$ is —C(=O)—, $CH_2$, O, S, or N$R^a$, preferably —C(=O)—, $CH_2$, or O, provided that when $L^1$ is —C(=O)—; $L^4$ is $CH_2$, O, S, or N$R^a$; when $L^4$ is —C(=O)—, $L^1$ is $CH_2$, O, S, or N$R^a$; and when $L^3$ is —C(=O)—, $L^1$ is =C($R^6$)—or —CH($R^6$)—, and $L^4$ is O or N$R^a$. Additionally, when $L^1$ is =C($R^6$)—, $L^2$ is =C—; when $L^1$ is —CH($R^6$)—, $L^2$ is —CH—; when $L^3$ is =C($R^6$)—, $L^2$ is =C—; and when $L^3$ is —CH($R^6$)—. $L^2$ is —CH—. = represents a single bond or double bond, depending upon the hybridization of $L^1$–$L^4$. The structures for $L^2$ show only three bonds because the fourth bond is a single bond to $R^1$.

$R^1$ is attached via a single bond to $L^2$, and is phenyl, substituted phenyl, Het, or substituted Het, as defined below. $R^1$ is preferably:

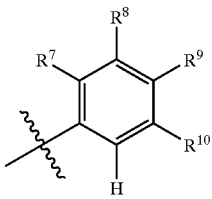

wherein: $R^7$ is H, Cl, or methyl; $R^8$ is Br, Cl, F, $R^a$, O$R^a$, or allyl; $R^9$ is H, OH, $NH_2$, Br, Cl; and $R^{10}$ is H or methyl: or $R^8$ and $R^9$ may combine to be —$OCH_2O$—, forming a secondary 5-membered ring structure exterior to the phenyl group; or $R^1$ is a substituted or unsubstituted heterocyclic substituent having the following structure:

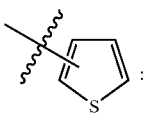

more preferably unsubstituted

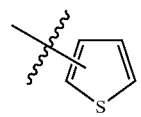

$R^2$, $R^3$, $R^4$, and $R^5$ are each independently, —$R_a$, —$OR_a$, —S$R^a$, —N$R^aR^a$, —NC(=O)$R^a$, —NS(=O)$R^a$, —NS(=O)$_2R^2$, halogen, cyano. —$CF_3$, —$CO_2R^a$, —C(=O)$R^a$, —C(=O)NH$R^a$, nitro, —S(=O)$R^a$, or —S(=O),$R^a$, and is preferably $R^a$, O$R^a$, $NR^2_a$, NC(=O)$R^a$, $CF_3$, or halogen, preferably, hydrogen, hydroxyl or methyl.

$R^6$ is $R^a$, phenyl or $CF_3$.

$R^a$ is, independently, at each occurrence, H or ($C_1$–$C_5$) alkyl.

When $L^1$ is —C(=O)—, and $R^2$ is hydroxy or hydrogen, and $R^3$ is hydrogen, and $R^4$ is hydroxy, and $R^5$ is hydrogen, and $R^6$ is hydrogen, then $R^1$ is not para-phenol.

For purposes of this invention, "substituted" when used to modify a phenyl or a heteroatomic ring means such a ring substituted at one or more positions, independently, with —$R^a$, —O$R^a$, —S$R^a$, —N$R^a$, $R^a$, —NC(=O)$R^a$, —NS(=O)$R^a$, —NS(=O)$_2$, $R^a$, halogen, cyano, —$CF_3$, —$CO_2R^a$, —C(=O)$R^a$, —C(=O)NH$R^a$, nitro, —S(=O)$R^a$, or —S(=O)$_2R^a$.

Also, for purposes of this invention, "Het" means a substituted or unsubstituted one- or two-ring heterocycle selected from the following:

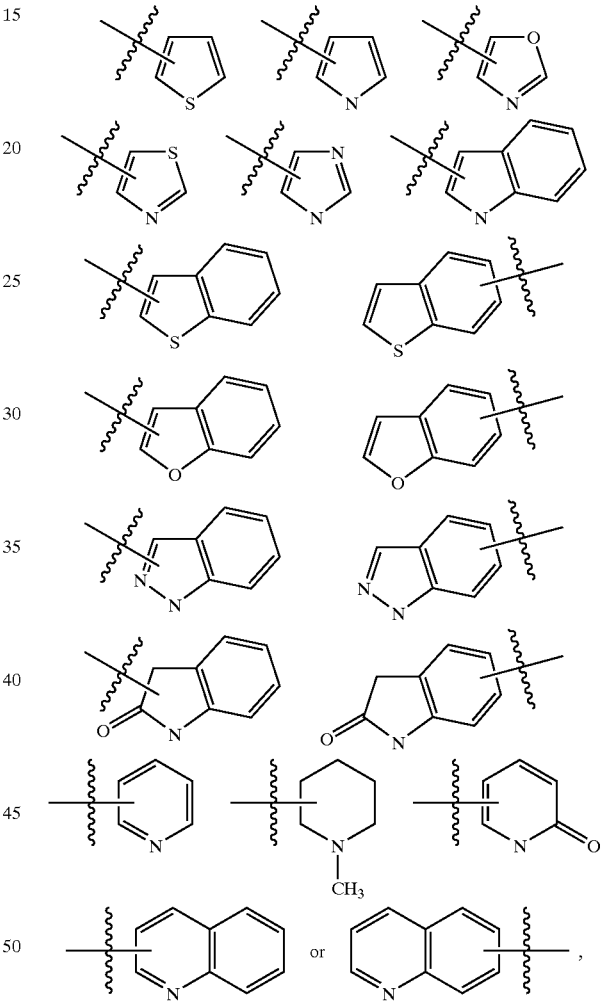

wherein the crossed bond represents that the heterocycle may be attached at any available position on the ring that it crosses.

ESTROGEN RECEPTOR BINDING MEASUREMENTS

The ability of a compound to bind to ER was measured by its ability to compete for binding with the radio-labeled estrogen. [$^{125}$I]-16α-iodo-3,17β-estradiol (NEN, Cat.#NEX-144). The radio-ligand is hereafter referred to as [$^{125}$I]-estradiol.

ER-β (Gen Bank Accession #X99101) or ER-α (Gen Bank Accession #M12674) cDNAs were cloned into the expression vector pSG5 (Stratagene), transformed into e.

coli strain DHαF', and purified using anion-exchange resin columns (Qiagen Cat.#12125). Receptor protein was prepared by in vitro transcription and translation of these plasmids using the TNT T7 Quick-Coupled reticulocyte lysate system (Promega Cat.#L1170). Reticulocyte lysate (12.5 mL) was incubated for 90 min at 30° C. with 312.5 μg of ER-α and 625 μg of ER-β plasmids. Programmed lysate was then aliquotted and stored frozen at −80° C.

Compounds were tested in duplicate at half-log concentrations ranging from 10 pM to 13 μM. Compounds were prepared as 1 mM stocks in DMSO, then diluted in the binding-assay buffer (in mM: 20 HEPES, 150 NaCl, 1 EDTA, 6 monothioglycerol and 10 $Na_2MoO_4$; 10% wt/vol glycerol, and pH =7.9) to a series of three-fold concentrated, 20 μL aliquots in a 96-well plate. Receptor aliquots were thawed on ice, and appropriately diluted (see below) in binding assay buffer. Diluted receptor (30 μL/each) was added to each well. [$^{125}$I]-estradiol was diluted from the manufacturer's ethanol stock solution to a 900 pM working solution in binding-assay buffer. The final assay volume was 60 μL, consisting of 20 μL of a compound according to the instant invention, 30 μL of programmed reticulocyte lysate, and 10 μL of 900 pM [$^{125}$I]-estradiol. The final concentration of [$^{125}$I]-estradiol was 150 pM. Plates containing the final assay mixture were mixed on a shaker for 2 min and incubated overnight (~16 h) at 4° C.

Receptor-bound and unbound radioligand was separated by filtration over sephadex columns. Columns (45 μL bed volume) were prepared by adding dry column media (Pharmacia Cat#G-25) to 96-well column templates (Millipore MultiScreen Plates Cat#MAHVN4510). Columns were then saturated with 300 μL of binding-assay buffer and stored at 4° C. Prior to use, stored columns were spun for 10 minutes at 2000 RPM, then washed twice with 200 μL of fresh binding buffer. The binding-assay mixtures (50 μL/each) were then applied to the columns, and an additional elution volume of 35 μL was immediately applied to the column. Receptor-bound radioligand was then eluted from the column by centrifugation for 10 minutes at 2000 RPM. A scintillation cocktail (145 μL) was added to the eluted radioligand/receptor complex, and radio-label was measured by liquid scintillation counting.

Non-specific binding was defined by competition with 150 nM diethylstilbesterol (DES) Binding affinities are expressed as $K_i$, calculated using the Cheng-Prushoff formula according to $IC_{50}$ values generated by fitting the relationship of concentration to percent specific binding (SB) with the following equation:

% SB=Maximum−(Maximum−Minimum)/(1+10 (logIC50-log[compound])) In this assay, standard estrogen receptor ligands estradiol and DES were detected as high-affinity ($K_i$<1 nM), non-selective ligands of ER-β and ER-α.

The volume of receptor-programmed reticulocyte lysate to be added to the binding assay was determined independently from two measurements made on each batch of receptor prepared. First, $K_i$s were determined for standard compounds using a series of dilutions of the receptor preparation. Scatchard analysis of ligand binding affinity was performed at the receptor dilutions that produced reported $K_i$s for these compounds and an acceptable signal:noise ratio (~10). These experiments indicated a $K_D$ for [$^{125}$I]-estradiol of 0.1–1 nM, and a $B_{max}$ of 5–30 pmol.

ADMINISTRATION AND USE

Compounds of the present invention are shown to have high selectivity for ER-β over ER-α, and may possess agonist activity on ER-β without undesired uterine effects. Thus, these compounds, and compositions containing them, may be used as therapeutic agents in the treatment of various CNS diseases related to ER-β, such as, for example. Alzheimer's disease.

The present invention also provides compositions comprising an effective amount of compounds of the present invention, including the nontoxic addition salts, amides and esters thereof, which may, serve to provide the above-recited therapeutic benefits. Such compositions may also be provided together with physiologically-tolerable liquid, gel or solid diluents, adjuvants and excipients. The compounds of the present invention may also be combined with other compounds known to be used as therapeutic agents for the above or other indications.

These compounds and compositions may be administered by qualified health care professionals to humans in a manner similar to other therapeutic agents and, additionally, to other mammals for veterinary use, such as with domestic animals. Typically, such compositions are prepared as injectables, either as liquid solutions or suspensions; solid forms suitable for solution in, or suspension in, liquid prior to injection may also be prepared. The preparation may also be emulsified. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents stabilizing or pH-buffering agents, and the like.

The compositions are conventionally administered parenterally, by injection, for example, either subcutaneously or intravenously. Additional formulations which are suitable for other modes of administration include suppositories, intranasal aerosols, and, in some cases, oral formulations. For suppositories, traditional binders and excipients may include, for example, polyalkylene glycols or triglycerides; such suppositories may be formed from mixtures containing the active ingredient. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders.

The present compounds may be formulated into the compositions as neutral or salt forms. Pharmaceutically-acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In addition to the compounds of the present invention that display ER-β activity, compounds of the present invention can also be employed as intermediates in the synthesis of such useful compounds.

SYNTHESIS

Compounds within the scope of the present invention may be synthesized chemically by means well known in the art.

The following Examples are meant to show general synthetic schemes, which may be used to produce many different variations by employing various commercially-available starting materials. These Examples are meant only as guides on how to make some compounds within the scope of the invention, and should not be interpreted as limiting the scope of the invention.

EXAMPLES

Example 1 (Route A)

(3-Bromo-4-hydroxyphenyl)-5,7-dihydroxy-4H-1-benzopyran-4-one 1,3.5-Trihydroxybenzaldehyde (1.01 g, 6.95 mmol) and 3-bromo-4-hydroxyphenylacetic acid (1.44 g, 6.25 mmol) were suspended in $POCl_3$ (4 mL). After 1 min, an exothermic reaction occurred. The mixture was allowed to cool to room temperature. Zinc chloride (1M ether solution, 4.7 mmol) was added and the mixture was heated at 75° C. for 1 h. After cooling, the mixture was partitioned in ethyl acetate and 1 M aqueous HCl. The organic layer was washed with brine and dried with $MgSO_4$. Purification on silica gel (MeOH/dichloromethane, gradient) afforded 1-(2,4,6-trihydroxyphenyl)-2-(3-bromo-4-hydroxyphenyl)ethanone (390 mg) as a tan solid.

To 1-(2,4.6-trihydroxyphenyl)-2-(3-bromo-4-hydroxyphenyl)ethanone (370 mg) in DMF (5 mL) under nitrogen was added $BF_3$-$Et_2O$ (0.83 mL, 6.55 mmol) dropwise, followed by methanesulfonyl chloride (0.507 mL, 6.55 mmol). The mixture was stirred at room temperature for 10 min and heated at 55° C. for 30 min. After cooling, the mixture was partitioned in ethyl acetate/1M aqueous HCl. The organic layer was washed with 1M HCl and brine, and purified by $C_{18}$ HPLC to give the title compound (55 mg).

Example 2 (Compound No. 28; Route B)

3-(4-hydroxyphenyl)-7-hydroxy-4-methylcoumarin

A solution of 2,4-dihydroxyacetophenone (1.1 g, 7.24 mmol). 4-hydroxyphenylacetic acid (1.45 g, 9.5 mmol) and potassium acetate (0.9 g. 9.2 mmol) in acetic anhydride (10 mL) was heated under reflux for 18 h. After cooling, the mixture was poured into ice and water. The solid was filtered, washed with ether and dried under vacuum to give 3-(4-acetoxyphenyl)-7-acetoxy-4-methylcoumarin (1.83 g).

A suspension of 3-(4-acetoxyphenyl)-7-acetoxy-4-methylcoumarin (500 mg) in THF (10 mL) and 1N aqueous sodium hydroxide (10 mL) was stirred for 1 h. The mixture is acidified to pH=1 with concentrated HCl and extracted with EtOAc 1 water. The organic layer was washed with brine and dried over $MgSO_4$. Evaporation of the solvent and trituration of the residue with ether gave the title compound (140 mg)

The HPLC conditions (HPLC 4.6×250 mm $C_{18}$ 5 μm Vydax 218TP54 column, flow rate: 1.5 mL/min, acetonitrile/water 0.1% TFA linear gradient from 10:90 to 50:50 over 30 min, UV detection: 254 nm) are referred as conditions A.

The HPLC conditions (HPLC 2.1×30 mm $C_{18}$ 3.5 μm Zorbax Rapid Resolution column, flow rate: 0.7 mL/min, water–0.05% TFA for 0.5 min, then 90% aqueous acetonitrile/water 0.05% TFA linear gradient from 0:100 to 80:20 over 9.5 min. UV detection) are referred as conditions B.

The following compounds were prepared according to these routes, using the relevant starting materials.

TABLE 1

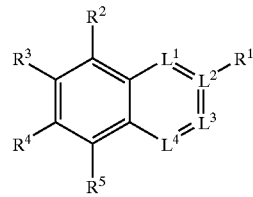

| No. | $L^1$ | $L^2$ | $L^3$ | $L^4$ | $R^1$ |
|---|---|---|---|---|---|
| 1 | C(=O) | =C— | =CR$^6$— | O | 3,4-dihydroxyphenyl |
| 2 | C(=O) | =C— | =CR$^6$— | O | 2-Cl-4-hydroxyphenyl |
| 3 | C(=O) | =C— | =CR$^6$— | O | 2-Me-4-hydroxyphenyl |
| 4 | C(=O) | =C— | =CR$^6$— | O | 3-F-4-hydroxyphenyl |
| 5 | C(=O) | =C— | =CR$^6$— | O | 3-Cl-4-hydroxyphenyl |
| 6 | C(=O) | =C— | =CR$^6$— | O | 3-Br-4-hydroxyphenyl |
| 7 | C(=O) | =C— | =CR$^6$— | O | 3-allyl-4-hydroxyphenyl |
| 8 | C(=O) | =C— | =CR$^6$— | O | 3-Pr-4-hydroxyphenyl |
| 9 | C(=O) | =C— | =CR$^6$— | O | 3-methoxy-4-hydroxyphenyl |
| 10 | C(=O) | =C— | =CR$^6$— | O | 3,5-diMe-4-hydroxyphenyl |
| 11 | C(=O) | =C— | =CR$^6$— | O | 4-fluorophenyl |
| 12 | C(=O) | =C— | =CR$^6$— | O | 3,4-(OCH$_2$O)phenyl |
| 13 | C(=O) | =C— | =CR$^6$— | O | 4-aminophenyl |
| 14 | C(=O) | =C— | =CR$^6$— | O | 2-naphthyl |
| 15 | C(=O) | =C— | =CR$^6$— | O | 3-hydroxyphenyl |
| 16 | C(=O) | =C— | =CR$^6$— | O | 2-hydroxyphenyl |
| 17 | C(=O) | =C— | =CR$^6$— | O | 2-thiophene |
| 18 | C(=O) | =C— | =CR$^6$— | O | 3-thiophene |
| 19 | C(=O) | =C— | =CR$^6$— | O | 2-quinolinyl |
| 20 | C(=O) | =C— | =CR$^6$— | O | 4-bromophenyl |
| 21 | C(=O) | =C— | =CR$^6$— | O | 4-chlorophenyl |
| 22 | C(=O) | =C— | =CR$^6$— | O | 4-hydroxyphenyl |
| 23 | C(=O) | =C— | =CR$^6$— | O | 4-hydroxyphenyl |
| 24 | C(=O) | =C— | =CR$^6$— | O | 3-F-4-hydroxyphenyl |
| 25 | C(=O) | =C— | =CR$^6$— | O | 4-hydroxyphenyl |
| 26 | C(=O) | —CH— | —CHR$^6$— | O | 4-hydroxyphenyl |
| 27 | C(=O) | —CH— | —CHR$^6$— | CH$_2$ | 4-hydroxyphenyl |
| 28 | =CR$^6$— | =C— | C(=O) | O | 4-hydroxyphenyl |
| 29 | =CR$^6$— | =C— | C(=O) | O | 4-hydroxyphenyl |
| 30 | =CR$^6$— | =C— | C(=O) | O | 4-hydroxyphenyl |
| 31 | =CR$^6$— | =C— | C(=O) | O | 2-thiophene |
| 32 | C(=O) | =C— | =CR$^6$— | O | 4-hydroxyphenyl |
| 33 | C(=O) | =C— | =CR$^6$— | O | 2-F-phenyl |
| 34 | C(=O) | =C— | =CR$^6$— | O | phenyl |
| 35 | C(=O) | =C— | =CR$^6$— | O | phenyl |
| 36 | O | =C— | =CR$^6$— | C(=O) | 4-hydroxyphenyl |
| 37 | CH$_2$ | —CH— | —CHR$^6$— | C(=O) | 4-hydroxyphenyl |
| 38 | =CR$^6$— | =C— | C(=O) | O | 4-hydroxyphenyl |
| 39 | =CR$^6$— | =C— | C(=O) | O | 4-hydroxyphenyl |
| 40 | =CR$^6$— | =C— | C(=O) | O | 4-hydroxyphenyl |
| 41 | =CR$^6$— | =C— | C(=O) | O | 4-hydroxyphenyl |
| 42 | =CR$^6$— | =C— | C(=O) | O | 4-Cl-phenyl |
| 43 | =CR$^6$— | =C— | C(=O) | O | 4-hydroxyphenyl |
| 44 | C(=O) | =C— | =CR$^6$— | O | 4-isopropoxyphenyl |
| 45 | C(=O) | —CH— | —CHR$^6$— | CH$_2$ | 3-Br-phenyl |
| 46 | CH$_2$ | —CH— | —CHR$^6$— | O | 4-hydroxyphenyl |

TABLE 1-continued

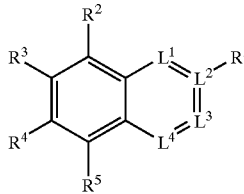

| No. | R² | R³ | R⁴ | R⁵ | R⁶ |
|---|---|---|---|---|---|
| 1 | OH | H | OH | H | H |
| 2 | OH | H | OH | H | H |
| 3 | OH | H | OH | H | H |
| 4 | OH | H | OH | H | H |
| 5 | OH | H | OH | H | H |
| 6 | OH | H | OH | H | H |
| 7 | OH | H | OH | H | H |
| 8 | OH | H | OH | H | H |
| 9 | OH | H | OH | H | H |
| 10 | OH | H | OH | H | H |
| 11 | OH | H | OH | H | H |
| 12 | OH | H | OH | H | H |
| 13 | OH | H | OH | H | H |
| 14 | OH | H | OH | H | H |
| 15 | OH | H | OH | H | H |
| 16 | OH | H | OH | H | H |
| 17 | OH | H | OH | H | H |
| 18 | OH | H | OH | H | H |
| 19 | OH | H | OH | H | H |
| 20 | OH | H | OH | H | H |
| 21 | OH | H | OH | H | H |
| 22 | OH | H | OMe | H | H |
| 23 | Me | H | OH | H | H |
| 24 | H | H | OH | H | H |
| 25 | H | H | OH | H | CF₃ |
| 26 | OH | H | OH | H | H |
| 27 | OH | H | OH | H | H |
| 28 | H | H | OH | H | Me |
| 29 | H | H | OH | H | Et |
| 30 | H | H | H | H | H |
| 31 | H | H | OH | H | H |
| 32 | OH | H | OH | OMe | H |
| 33 | OH | H | OH | H | H |
| 34 | OH | H | OH | H | Ph |
| 35 | H | H | OH | H | Ph |
| 36 | H | H | OH | H | H |
| 37 | H | H | OH | H | H |
| 38 | H | H | OH | H | H |
| 39 | OH | H | OH | H | H |
| 40 | H | H | H | OH | H |
| 41 | H | OH | H | H | H |
| 42 | H | H | OH | H | Me |
| 43 | H | H | OH | Me | Me |
| 44 | H | H | OH | H | CF₃ |
| 45 | H | H | OH | H | H |
| 46 | H | H | OH | H | H |

TABLE 2

Purification, Properties, and Synthetic Route

| No. | HPLC min (method) | MS(MH⁺) | ER-β $K_i$ nM | ER-α $K_i$ nM | Synthetic Route |
|---|---|---|---|---|---|
| 1 |  |  | 2.15 | 605 | * |
| 2 | 5.76(B) | 305(³⁵Cl) | 0.55 | 56 | A |
| 3 | 5.41(B) | 285 | 1.2 | 61 | A |
| 4 | 5.62(B) | 289 | 0.5 | 74 | A |
| 5 | 6.11(B) | 305(³⁵Cl) | 1.2 | 1100 | A |
| 6 | 25.6(A) | 349(³⁹Br) | 1.25 | 439 | A |
| 7 | 6.72(B) | 311 | 3.2 | >3000 | A |
| 8 | 7.08(B) | 313 | 0.75 | >3000 | A |
| 9 |  |  | 143 | >3000 | * |

TABLE 2-continued

Purification, Properties, and Synthetic Route

| No. | HPLC min (method) | MS(MH⁺) | ER-β $K_i$ nM | ER-α $K_i$ nM | Synthetic Route |
|---|---|---|---|---|---|
| 10 | 25.4(A) | 299 | 25 | >3000 | A |
| 11 | 6.93(B) | 273 | 100 | >3000 | A |
| 12 |  |  | 22 | >3000 | * |
| 13 |  |  | 6 | >3000 | * |
| 14 | 7.86(B) | 305 | 150 | >3000 | A |
| 15 | 5.39(B) | 271 | 15 | 900 | A |
| 16 | 5.68(B) | 271 | 110 | >3000 | A |
| 17 | ¹H NMR(DMSO-d₆): 12.59(s, 1H), 10.99(s, 1H), 8.88(s, 1H), 7.63(m, 2H), 7.14(m, 1H), 6.44(s, 1H), 6.27(s, 1H). | | 3.3 | >3000 | A |
| 18 | ¹H NMR(DMSO-d₆): 12.92(s, 1H), 10.93(s, 1H), 8.72(s, 1H), 8.07(s, 1H), 7.64(m, 1H), 7.53(m, 1H), 6.42(s, 1H), 6.24(s, 1H). | | 17 | >3000 | A |
| 19 | 5.26(B) | 306 | 122 | >3000 | A |
| 20 | 7.70(B) | 333(⁷⁹Br) | 25 | >3000 | A |
| 21 | 7.55(B) | 289(³⁵Cl) | 42 | >3000 | A |
| 22 |  |  | 50 | >3000 | * |
| 23 | 5.20(B) | 269 | 0.5 | 200 | A |
| 24 | 4.91(B) | 273 | 3.3 | >3000 | A |
| 25 | 6.07(B) | 323 | 10 | 321 | Note a) |
| 26 |  |  | 3.7 | 1000 | * |
| 27 | 5.43(B) | 271 | 5.7 | 3000 | Note b) |
| 28 | ¹H NMR(DMSO-d₆): 10.47(m, 1H), 9.55(m, 1H), 7.67(d, 1H), 7.1–6.7(m, 6H), 2.22(m, 3H); MS: 269 | | 12 | 322 | B |
| 29 | 5.57(B) | 283 | 4 | 80 | B |
| 30 | 6.01(B) | 239 | 140 | >3000 | B |
| 31 | ¹H NMR(DMSO-d₆): 10.68(s, 1H), 8.44(s, 1H), 7.75(m, 1H), 7.60(m, 2H), 7.16(m, 1H), 6.87(dd, 1H), 6.81(m, 1H); MS: 245 | | 108 | >3000 | B |
| 32 |  |  | 33 | >3000 | * |
| 33 | ¹H NMR(DMSO d-6): 12.66(s, 1H), 10.98(s, 1H), 8.42(s, 1H), 7.48(m, 2H), 7.27(m, 2H), 6.44(d, 1H, J=2.1Hz), 6.26(d, 1H, J=2.1Hz); MS: 273 | | 50 | >3000 | A |
| 34 |  |  | 9.5 | 95 | * |
| 35 |  |  | 19 | 50 | * |
| 36 |  |  | 0.33 | 88 | * |
| 37 | ¹H NMR(DMSO d-6): 9.61(s, 1H), 9.52(s, 1H), 7.26(d, 1H J=2.7Hz), 7.21–7.13(m, 3H), 6.99(dd, 1H, J=8.1Hz, J'=2.7Hz), 6.71(d, 2H, J=8.4Hz), 3.26(m, 1H), 3.07–2.80(m, 3H), 2.64(m, 1H); MS: 253(M-H)⁺ | | 0.73 | 75 | Note c) |
| 38 | ¹H NMR(DMSO d-6): 10.52(s, 1H), 9.64(s, 1H), 8.03(s, 1H), 7.55(m, 3H), 6.85–6.70(m, 4H); MS: 255 | | 4.9 | 220 | B |
| 39 | ¹H NMR(DMSO d-6): 10.63(s, 1H), 10.33(s, 1H), 9.60(s, 1H), 7.95(s, 1H), 7.50(d, 2H, J=8.4Hz), 6.80(d, 2H, J=8.4Hz), 6.28(s, 1H), 6.22(s, 1H); MS: 271 | | 79 | >3000 | B |
| 40 | ¹H NMR(DMSO d-6): 10.18(s, 1H), 9.73(s, 1H), 8.08(s, 1H), 7.60(d, 2H, J=8.4Hz), 7.17(m, 2H), 7.06(m, 1H), 6.85(d, 2H, J=8.4Hz); MS: 255 | | 104 | >3000 | B |
| 41 | ¹H NMR(DMSO d-6): 9.72(s, 2H), 8.05(s, 1H), 7.58(d, 2H, J=8.4Hz), 7.25(d, 1H, J=8.7Hz), 7.07(d, 1H, J=2.7Hz), 7.00(dd, 1H, J=8.4Hz, J'=2.7Hz), 6.84(d, 2H, J=8.4Hz); MS: 255 | | 4.6 | 3000 | B |

TABLE 2-continued

Purification, Properties, and Synthetic Route

| No. | HPLC min (method) | MS(MH+) | ER-β $K_i$ nM | ER-α $K_i$ nM | Synthetic Route |
|---|---|---|---|---|---|
| 42 | $^1$H NMR(DMSO d-6): 10.56(s, 1H), 7.50(d, 2H, J=7.8Hz), 7.42(d, 1H, J=8.7Hz), 7.33(d, 2H, J=7.8Hz), 6.84(dd, 1H, J=7.8Hz, J'=2.1Hz), 6.75(d, 1H, J=2.1Hz), 2.21(s, 3H); MS: 287($^{35}$Cl) | | 51 | >3000 | B |
| 43 | $^1$H NMR(DMSO d-6): 10.36(s, 1H), 9.55(s, 1H), 7.49(d, 1H, J=9Hz), 7.08(d, 2H, J=8.7Hz), 6.87(d, 1H, J=9Hz), 6.81(d, 2H, J=8.7Hz), 2.21(s, 3H), 2.19(s, 3H); MS: 283 | | 24 | 500 | B |
| 44 | $^1$H NMR(DMSO d-6): 11.11(s, 1H), 7.93(d, 1H, J=8.7Hz), 7.16(d, 2H, J=8.4Hz), 7.03–6.93(m, 4H), 4.66(m, 1H), 1.30(d, 6H, J=6Hz); MS: 365 | | 118 | 3000 | Note a) |
| 45 | $^1$H NMR(DMSO d-6): 10.39(s, 1H), 7.78(d, 1H, J=8.4Hz), 7.42(m, 2H), 7.28(t, 1H, J=7.8 Hz), 7.19(d, 1H, J=7.8Hz), 6.75(dd, 1H, J=8.4Hz, J'=2.4Hz), 6.69(d, 1H, J=2.4Hz), 3.86(m, 1H), 3.00(m, 1H), 2.85(m, 1H), 2.4–2.1(m, 2H); MS: 317($^{79}$Br) | | 116 | 3000 | Note b) |
| 46 | | | 2 | 155 | * |

*compound is commercially available.
Note a): Prepared according to method A; the cyclization step was done using trifluoroacetic anhydride according to J. Med. Chem. 1992, 35, 3519.
Note b): Prepared by cyclization of the corresponding 2,4-diarylbutyric acid with POCl$_3$, and subsequent demethylation of the methoxy ethers according to the method developed in J. Org. Chem. 1946 11, 34.
Note c): Prepared according to Aust. J. Chem. 1978, 31, 1011.

What is claimed is:

1. A method of treating a disease associated with the estrogen receptor-β, comprising the step of administering a therapeutically-effective amount of a compound that has the formula:

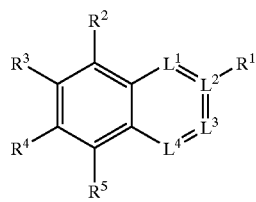

wherein:
  $L^1$ is =C($R^6$)—, —CH($R^6$)—;
  $L^2$ is =C— or —CH—;
  $L^3$ is —C(=O)—;
  $L^4$ is O
  wherein:
    when $L^1$ is =C($R^6$)—, $L^2$ is =C—; and
    when $L^1$ is —CH($R^6$)—, $L^2$ is —CH—;
  $R^a$ is, independently, at each occurrence, H or ($C_1$–$C_5$) alkyl;
  $R^1$ is phenyl, substituted phenyl or Het;
  $R^2$, $R^3$, $R^4$ and $R^5$ are independently selected from the group consisting of —$R^a$, —O$R^a$, —S$R^a$, —N$R^a R^a$, —NC(=O)$R^a$, —NS(=O)$R^a$, —NS(=O)$_2 R^a$, halogen, cyano, —CF$_3$, —CO$_2 R^a$, —C(=O)$R^a$, —C(=O)NH$R^a$, nitro, —S(=O)$R^a$ and —S(=O)$_2 R^a$;
  $R^6$ is H, ($C_1$–$C_5$) alkyl, phenyl or CF$_3$; or a pharmaceutically acceptable salt thereof.

2. The method according to claim 1, wherein the disease to be treated is selected from the group consisting of Alzheimer's disease, anxiety disorders, depressive disorders, osteoporosis, cardiovascular disease, rheumatoid arthritis and prostate cancer.

3. The method according to claim 1, wherein $R^1$ is Het.

4. The method according to claim 1, wherein:

$R^1$ has the structure:

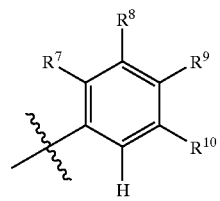

wherein:
  $R^7$ is H, Cl or methyl;
  $R^8$ is Br, Cl, F, $R^a$, O$R^a$ or allyl;
  $R^9$ is H, OH, NH$_2$, Br or Cl; and
  $R^{10}$ is H or methyl; or
  $R^8$ and $R^9$ combine to form —OCH$_2$O—; or $R^1$ is a substituted or unsubstituted version of one of the following:

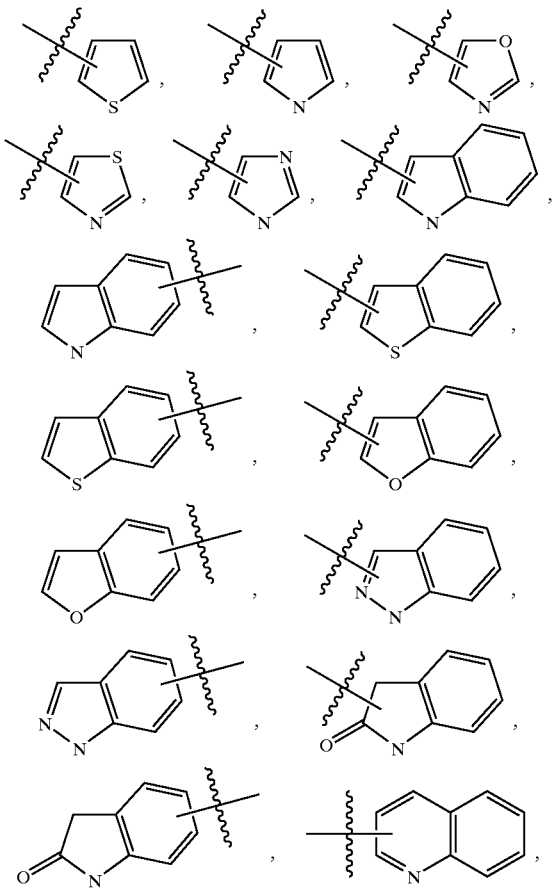

-continued

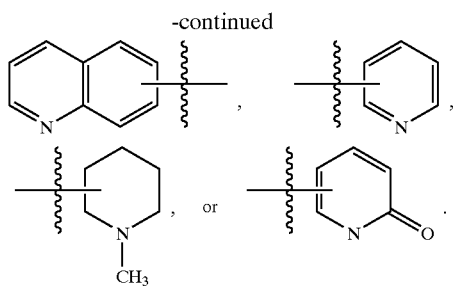
, or

5. The method according to claim 1 wherein $R^2$, $R^3$, $R^4$ and $R^5$ are independently selected from the group consisting of $R^a$, $OR^a$, $NR^a_2$, $NC(=O)R^a$, $CF_3$ and halogen.

6. The method according to claim 1 wherein:
$R^2$ is hydroxyl or hydrogen;
$R^3$ is hydrogen or methyl;
$R^4$ is hydroxyl or hydrogen; and
$R^5$ is hydrogen or hydroxyl.

7. The method according to claim 1 wherein $R_1$ is an unsubstituted version of

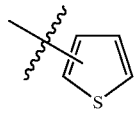

* * * * *